United States Patent [19]

De Munck

[11] Patent Number: 5,071,572

[45] Date of Patent: Dec. 10, 1991

[54] PRODUCTION OF ALCOHOLS

[75] Inventor: Nicolaas A. De Munck, Barendrecht, Netherlands

[73] Assignee: Exxon Chemical Patents Inc., Linden, N.J.

[21] Appl. No.: 403,305

[22] Filed: Sep. 1, 1989

[30] Foreign Application Priority Data

Sep. 2, 1988 [GB] United Kingdom ............. 8820746

[51] Int. Cl.$^5$ .................... C09K 00/00; C07C 45/00
[52] U.S. Cl. ...................................... 252/1; 568/451; 568/883
[58] Field of Search .................... 252/1; 524/376; 568/881, 882, 883, 594, 451, 452

[56] References Cited

U.S. PATENT DOCUMENTS

| | | | |
|---|---|---|---|
| 4,400,299 | 8/1983 | Lagace et al. | 252/413 |
| 4,401,834 | 8/1983 | King | 568/881 |
| 4,647,707 | 3/1987 | Van Vliet | 568/882 |
| 4,656,215 | 4/1987 | Hanin et al. | 524/376 |
| 4,658,068 | 4/1987 | Hanin | 568/451 |
| 4,683,343 | 7/1987 | Hanin et al. | 568/594 |
| 4,735,745 | 8/1988 | Hanin et al. | 252/364 |

Primary Examiner—John S. Maples
Assistant Examiner—Shean C. Wa
Attorney, Agent, or Firm—J. J. Mahon

[57] ABSTRACT

In the the oxo process for alcohol production the heavy component left after enriching and recycling is itself recycled to oxonation to give yield improvement.

2 Claims, No Drawings

PRODUCTION OF ALCOHOLS

This invention relates to the production of alcohols by hydroformylation processes and in particular the production of alcohols of high purity by a simplified process.

The hydroformylation process, in general terms, is a process involving the preparation of oxyqenated organic compounds by the reaction of carbon monoxide and hydrogen (synthesis gas) with carbon compounds containing olefinic unsaturation. The reaction is performed under hydroformylation conditions in the presence of a carbonylation catalyst or catalyst precursor such as dicobaltoctacarbonyl, and results in the formation of a compound e.g. an aldehyde which has one more carbon atom in its molecular structure than the feedstock. Subsequent hydrogenation of the primary product leads to higher alcohols which may be used for example for conversion into plasticizers.

Typically in higher alcohol production the feedstock for a hydroformylation process is a commercial $C_4$–$C_{16}$ preferably $C_6$–$C_{12}$ olefine fraction and the desired end product is the respective $C_5$–$C_{17}$ particularly $C_7$–$C_{13}$ saturated alcohol or derived mixed alcohol product, produced by hydrogenation of the aldehyde oxonation product. By virtue of the nature of the feedstock commonly available to industry, and indeed of the catalyst and reaction parameters employed, the oxonation..reaction yields a range of products due to the numerous secondary reactions which take place. The main commercial products of the hydroformylation reaction are aldehydes and alcohols, with side reactions in the oxonation demetalling and hydrogenation sections of the process system producing some 5 to 20 wt.% of high boiling materials by condensation, esterification and dehydration reactions.

In a conventional higher oxo alcohol process, the feedstock as described above is fed together with synthesis gas into an oxonation unit where catalytic hydroformylation takes place using e.g. hydrocobaltoctacarbonyl as the active catalyst species.

Oxonation of olefins produces as primary products aldehydes, alcohols and formate esters. During the course of oxonation aldehyde and alcohol react with each other to form a hemiacetal, which is converted into acetals and/or unsaturated ethers. The .unsaturated ethers.:, are converted by oxonation into ether-aldehydes and ether-alcohols, or by hydrogenation into saturated ethers. By convention the unsaturated and hydrogenated ethers are designated as "Reversibles", while the ether-aldehydes and ether-alcohols are called "Irreversibles".

After oxonation the product goes through a hydrogenation step to convert aldehydes into alcohols. During this process it is believed that at least a part of the unsaturated ethers and ether-aldehydes are hydrogenated as well.

The product mixture after hydrogenation comprising the higher alcohol, the high boiling materials mentioned above and a low boiling fraction is passed to a distillation unit where low boiling materials, high boiling materials and the desired alcohol product are separated. The Heavy Oxo Fraction (HOF), containing Reversibles, Irreversibles and acetals, are either disposed of or sent to Cracking (HOF Cracking). In the cracking process most of the Irreversibles and acetals are cracked to aldehyde and alcohols, while the Reversibles are hardly converted and remain as heavies.

The product coming out of the Cracking reactor is flashed, the light products go overhead, while the heavies stay in the bottom product (U-HOF). These heavies usually contain dimers such as ethers and ether-alcohols (e.g. $C_{20}$ compounds in $C_{10}$ alcohol production) and trimers such as acetals (e.g. $C_{30}$ compounds in $C_{10}$ alcohol production) and heavier; although substantially alcohol free (apart from the heavy ether-alcohols), it may contain a minor amount of alcohol which has not been removed in the distillation stage where the higher alcohol product of the hydroformylation process is separated. In European patent publication 0183545 we describe a process for upgrading these heavy fractions to more useful alcohol.

We have now found that it is possible to convert Reversible components present in the U-HOF into Irreversible components, which are crackable during the HOF cracking operation. This suggests that components inert during HOF cracking can be converted into crackable species, and lead to a further improvement of alcohol manufacturing economics.

Our experiments have shown that by recirculating U-HOF to Oxonation the production of Reversible components is suppressed or even totally avoided.,, Oxonation of mixtures of olefines particularly nonene with up to 30 wt.% preferably from 5 to 30 wt% U-HOF show a reduced heavies make compared to oxonation of nonene only.

The application of the invention is twofold. First by recirculation U-HOF back to Oxonation it is possible to minimize or to avoid net U-HOF production, provided HOF Crackinq is kept in operation. /The second option is to recirculate alcohol-ethers, derived after distillation of U-HOF, back to oxonation and convert them into the more valuable ether-aldehydes. .

The process is applicable to the production of alcohols from any linear or branched olefins which may be subjected to hydroformylation but is particularly suited to the hydroformylation of $C_4$ to $C_{16}$ especially $C_6$ to $C_{12}$ olefins for the production of $C_5$ to $C_{17}$ especially $C_7$–$C_{13}$ alcohols, our invention is particularly beneficial to the processing of $C_8$ to $C_{16}$ branched olefins since those tend to produce the most heavy material.

Conventional hydroformylation conditions may be used in the process of this invention. The catalyst may be for example cobalt based and the operating temperatures, pressures and other conditions such as synthesis gas composition may be controlled in accordance with the usual expertise of the person skilled in the art to maximise yield of the desired higher alcohol product. For example the hydroformylation reaction may be carried out at a pressure of 150–300 atm, and a temperature of 120–190° C.

The catalyst may be used in desired active form, for example in a concentration of from 0.05–3 wt% preferably 0.05 and 1 wt % as metal based on the olefinic feed.

Typically the synthesis gas used might have a $H_2$:CO volume ratio in the range 0.9:1–1.5:1. The catalyst is generally separated from the product mixture prior to the hydrogenation step.

The catalytic hydrogenation step is preferably carried out at a temperature in the range 150o to 240.C preferably 170° C. to 200° C. The preferred pressure of operation is in the 45–65 atm range. It has been found that the hydrogenation reaction to the desired alcohol enriched product mixture proceeds satisfactorily at a space velocity of from 0.2-2 vol/vol/hour, with the more preferred -space- velocity range being from 0.75-1.25 vol/vol/hour. By space velocity is meant the hourly flow by volume of the liquid reactants per unit volume of catalyst employed. The traditional hydrogenation catalysts may be employed such as the so-called copper chrome (also termed Cu/Cr or copper-chromium oxide or copper-chromite) catalysts and supported nickel; the present invention however enables sulphur tolerant regenerable catalysts such as cobalt/molybdenum, sulphided nickel/molybdenum, nickel/tungsten sulphided derivatives to be used in the hydrogenation step of the process.

The desired alcohol fraction typically contains up to 2 weight % carbonyl containing compounds particularly aldehydes and such an amount leads to poor colour and undesirable odours in plasticisers produced from the alcohols. The alcohol fraction is therefore generally subjected to hydrofinishing to reduce its carbonyl level.

This invention is illustrated by the following examples using decyl alcohol U-HOF obtained from a commercial plant.

In experiment 1 the U-HOF was oxonated, while in comparative experiment 2 the U-HOF was subject only to heat soaking. Experiment 3 describes the results of oxonation of a mixture of commercially available nonene stream produced by oligomerisation and U-HOF, (50/50 on a weight basis). Experiment 4 oxonates a 70/30 nonene/U-HOF mixture. Experiment 3 has been repeated and gave reproducible results. Experiment -5 which is comparative oxonates a mixture of HOF Cracking feed (virgin.-- HOF) and nonene (50/50 on a weight basis) the results in experiment 5 do not give the results as shown in Experiment 3. Experiment 6 compares the process of the invention with oxonation of a mixture of nonene and the light fraction derived after HOF cracking. Experiment 7 shows that the beneficial effect of U-HOF already occurs at low levels of U-HOF. Experiment 8, which is comparative, illustrates that $C_{20}$ ethers, although present U-HOF, do not give a positive effect as shown in experiments 3,4 and 7.

EXPERIMENT 1

1700 g of U-HOF, derived after oxonating nonene hydrogenating the OXO product and cracking the heavy fraction according to EP 0183545, is loaded into a batch oxo reactor and heated to 175° C., 300 g U-HOF containing dicobalt octacarbonyl catalyst (678 ppm Co in total mixture) is injected into the reactor with synthesis gas. The pressure is then raised to 290 bar and kept at that pressure, while maintaining a small synthesis gas flow through the reactor. At regular intervals samples are taken for GC-analysis. At the end of the reaction 3 wt% caustic is injected to neutralise the catalyst. After removal of the mixture from the reactor, separation of water and oil, 2052 g of product was recovered.

The results of the GC-analysis of the sample are listed in the attached Table 1.

The results of the test show, despite the low cobalt concentration, that Reversibles are converted into Irreversible species. The feed had a Reversible/Irreversible ratio of 1.54, the product ratio was 0.82 at approximately the same total Reversible + Irreversible concentration. This result is unexpected since the bromine index the U-HOF feed is very low (6.1 mg $Br_2$/100 g). The index is a measure for unsaturation (double carbon bonds), and despite the absence of double carbon bonds the ether components are oxonated into ether-aldehydes.

The table also shows the calculated olefin utilisation which is the amount of olefin feed required to produce 1 tonne of finished alcohol. Table 1 thus showing the improved efficiency by using the process of the invention, the utilisation dropping from 4.86 in the feed to 4.09 in the final product.

The method of calculation is that the corresponding moles of olefin converted to aldehydes, alcohols, formate esters and acetals are calculated from the GC results. The olefin utilisation, expressed in ton olefin per ton alcohol is then calculated by taking the inverse of the sum of moles olefin converted to aldehydes, alcohols, formate esters and acetals multiplied by the ratio of the olefin molecular weight and the alcohol molecular weight.

OLEFIN UTILISATION =

$$\left( \frac{100}{\text{mol \% olefin converted to alcohols, aldehydes, formates and acetals}} \right) \times$$

$$\left( \frac{\text{molecular wt olefin}}{\text{molecular wt alcohol}} \right)$$

EXPERIMENT 2

1700 g of the U-HOF used in Experiment 1 was loaded into the batch oxo reactor, heated to 200° C. and kept at 200° C. for 5 hours. The reactor was kept at 10 bar syngas pressure, while maintaining a small synthesis gas flow through the reactor. At regular intervals samples have been taken for GC-analysis.

The results of the GC analysis of the samples are listed on the attached Table 2. The feed acid number was 4.41 mg KOH/g, the saponification number 0.97 mg KOH/g, and the carbonyl number 35.31 mg KOH/g. For the final product these numbers were respectively 2.83, 0.27, 34.75 mg KOH/g.

The results of this experiment show a small increase in Reversible content and a small decrease of the Irreversible content. This is the opposite of the results obtained during oxonation, which means that in experiment I a thermal process is not responsible for the observed disappearance of Reversible components.

EXPERIMENT 3

1000 g U-HOF used in Example 1 and 700 g nonene are loaded into the batch oxo reactor and heated to 175° C.. 300 g none containing dicobalt octacarbonyl catalyst (2313 ppm Co in total mixture) is injected into the reactor with synthesis gas. The pressure is then raised to 285 bar and kept at that pressure, while maintaining a small synthesis gas flow through the reactor. At regular intervals samples have been taken for GC-analysis. At the end of the reactor after 3 hours 3 wt% caustic is injected to neutralize the catalyst. After removal of the mixture from the reactor, separation of water and oil phases, 2182 g of product was recovered (2210 g calculated).

The results of the GC-analysis of the samples are listed in Table 3. Also the olefin conversion as calculated from the GC-analysis and the potential alcohol yield or olefin utilization, tones of olefin necessary to produce 1 tone of finished alcohol, are given.

Based on the analysis of the feed 513 g Reversibles are present, the final product mixture after neutralization contains 408 g Reversibles indicating a net disappearance of 105 g Reversibles. The feed contained 338 g Irreversibles the product 642 g Irreversibles giving a production of 304 g Irreversibles. Oxonation of 1000 g pure nonene would give under the same experimental circumstances 32 g Reversibles and 163 g Irreversibles, clearly indicating the improved selectivity towards the formation of Irreversible products.

Calculation of olefin utilisation excluding the effect of HOF gives 1.10 tone olefin/tone alcohol for nonene oxonation in the presence of U-HOF vs 1.12 for pure nonene. This illustrates the positive yield effect of U-HOF during oxonation. As the selectivity towards crackable material has increased, the olefin utilisation after HOF cracking will further increase due to this improvement in selectivity

EXPERIMENT 4

600 g of the U-HOF used in Example 1 and 1100 g nonene are loaded into the batch oxo reactor and heated to 175° C.. 300 g nonene containing dicobalt octacarbonyl catalyst (2236 ppm Co in total mixture) is injected into the reactor with synthesis gas. The pressure is then raised to 285 bar and kept at that pressure, while maintaining a small synthesis gas flow through the reactor. At regular intervals samples have been taken for GC-analysis. At the end of the reaction after 3 hours 3 wt% caustic is injected to neutralise the catalyst. After removal of the mixture from the reactor, separation of water and oil phases, 2245 g of product was recovered (2308 g calculated).

The results of the GC-analysis of the samples are listed in Table 4. Also the olefin conversion and the olefin utilization are given.

Based on the analysis of the feed 337 g Reversibles are present, the final product mixture after neutralization contains 252 g Reversibles indicating a net disappearance of 85 g Reversibles. The feed contained 178 g Irreversibles, the product 458 g Irreversibles giving a production of 280 g Irreversibles. Oxonation of 1400 g pure nonene would give under the same experimental circumstances 45 g Reversibles and 231 g Irreversibles products. This again demonstrates the improved selectivity towards the formation of Irreversible products. This experiment also shows the reduced production of Reversible +Irreversible components 195 g for the mixture vs 276 g for nonene oxonation only. Calculation of olefin utilization excluding the effect of HOF cracking gives 1.07 tone olefin/tone alcohol, which illustrates the potential for yield improvement.

COMPARATIVE EXPERIMENT 5

1000g of HOF Cracking feed and 700g nonene are loaded into the batch of reactor and heated to 175 300g nonene containing dicobalt octacarbonyl catalyst F is (2110 ppm Co in total mixture) is injected into the reactor with synthesis gas. The pressure is then raised to 290 bar and kept at that pressure, while maintaining a small synthesis gas flow through the reactor. At regular intervals samples were taken for GC-analysis. At the end of the reaction, after 3 hours, 3 wt % caustic is injected to neutralize the catalyst. After removal of the mixture from the reactor, separation of water and oil phases, 2104g of product was recovered (2210g calculated).

The results of the GC analysis of the samples are listed in Table 5. Also the nonene conversion and the olefine utilization are given.

Based on the analysis of the feed 295g Reversibles are present, the final product mixture after neutralization contains 261g Reversibles, indicating a net disappearance of only 34g Reversibles (compared to 105g in experiment 3) The feed contained 574g Irreversibles the product 730g Irreversibles giving a production of 156g Irreversibles, Oxonation of 1000g pure nonene would give under the same experimental circumstances 32g Reversibles and 163g Irreversibles. The experiment shows the addition of the HOF cracking feed to nonene feed does not give the improved selectivity towards the formation of Irreversible products. It is also demonstrated that using the HOF cracking feed gives a lower disappearance of Reversibles than the addition of U-HOF.

EXPERIMENT 6

1000g light products, derived after cracking the HOF and separating from U-HOF, and 700g nonene are loaded into the batch oxo reactor and heated to 175.C 300g nonene containing dicobalt octacarbonyl catalyst (2070 ppm Co in total mixture) is injected into the reactor with synthesis gas. The pressure is then raised to 288 bar and kept at that pressure, while maintaining a small synthesis gas flow through the reactor. At regular intervals samples have been taken for GC-analysis. At the end of the reaction, after 3 hours, 3 wt % caustic is injected to neutralize the catalyst. After removal of the mixture from the reactor, separation of water and oil phases, 2161g of product was recovered (2223g calculated).

The results of the GC-analysis of the samples are listed in Table 6. Also the nonene conversion and the olefin utilization are given.

Based on the analysis of the feed 175g Reversibles are present, the final product mixture after neutralization contains 155g Reversibles indicating a net disappearance of 20g Reversibles. The feed contained 20g Irreversibles, the product 288g giving a production of 268g Irreversibles.

Calculation of olefin utilization gives 1.20 tonne olefin/tone alcohol for nonene oxonation in the presence of HOF cracked light products vs 1.12 for pure nonene.

This example illustrates that oxonating mixtures of nonene and HOF cracked alcohol gives an increased production of Irreversibles and a minor disappearance of Reversibles.

However, this coincides with a deterioration of the olefin utilization, whereas the addition of U-HOF gave a small improvement in olefin utilization.

EXPERIMENT 7

This experiment shows that the beneficial effect of U-HOF addition occurs at low levels of U-HOF, which are representative for a commercial plant operation.

200g U-HOF and 1500g nonene are loaded into the batch oxo reactor and heated to 175.C. 300g nonene containing dicobalt octacarbonyl catalyst (270 g ppm Co in total mixture) is injected into the reactor with synthesis gas. The pressure is then raised to 286 bar and kept at that pressure, while maintaining a small synthesis gas flow through the reactor. At regular intervals samples have been taken for GC-analysis. At the end of the reaction after 3 hours 2wt % caustic is injected to neutralize the catalyst. After removal of the mixture from the reactor, separation of water and oil phases, 2390 g of product was recovered (2396 g calculated).

The results of the GC-analysis of the samples are listed in Table 7. Also the nonene conversion and the olefin utilization are given.

Based on the analysis of the feed 112g Reversibles are present, the final product mixture after neutralization contains 123g Reversibles indicating a net production of 11g Reversibles. The feed contained 59g Irreversibles, while the product has 344g Irreversibles. This indicated that the formation of re is suppressed by the addition of 10% U-HOF to olefin feed.

The experiments 3 and 4 demonstrate at higher addition levels in addition to suppression of Reversibles formation, also an enhanced selectivity towards Irreversibles products. Furthermore, calculation of olefin utilization excluding the effect of HOF cracking gives 1.10 tone olefin/tone alcohol vs 1.12 for pure nonene. Hence, at low levels of U-HOF the olefin utilization is improved.

EXPERIMENT 8

In this experiment $C_{20}$ ethers were oxonated in a mixture with nonene. The $C_{20}$ ethers are components, which are designated Reversibles, derived by hydrogenating and distilling U-HOF.

1000g $C_{20}$ ethers and 700g nonene are loaded into the batch oxo reactor and heated to 175° C. 300g nonene containing dicobalt octacarbonyl catalyst (2150 ppm Co in total mixture) is injected into the reactor with synthesis gas. The pressure is then raised to 294 bar and kept at that pressure, while maintaining a small synthesis gas flow through the reactor. At regular intervals samples have been taken for GC-analysis. At the end of the reaction after 3 hours 3 wt % caustic is injected to neutralize the separation of water and oil phases, 2200 g of product was recovered (2210g calculated).

The results of the GC-analysis of the samples are listed in Table 8. Also the nonene conversion and the olefin utilization are given.

Based on the analysis of the feed 987g Reversibles are present, the final product mixture after neutralization contains 1091g Reversibles indicating a net production of 104g Reversibles. The feed contained no Irreversibles, while the product had 130g Irreversibles, net production is 180g. Total Reversibles and Irreversibles production is 234g, while 1000g pure nonene would have given 194g (32g Reversibles plus 163g Irreversibles).

Calculation of olefin utilization excluding the effect of HOF cracking gives 1.13 tone olefin/tone alcohol for nonene oxonation in the presence of C20 ethers vs 1.12 for pure nonene.

This example illustrates that C20 ethers, although present in the Reversibles of U-HOF, do not give the positive yield effect of U-HOF, during oxonation. In fact they produce more Reversibles, which are not crackable during HOF cracking and give a poorer olefin utilization.

In the Tables that follow the following abbreviations are used:

| | |
|---|---|
| Olef = | olefin |
| par = | paraffin |
| ald = | aldehyde |
| alc = | alcohol |
| for = | formates |
| rev = | reversibles |
| irrev = | irreversibles |
| acet = | acetals |
| heavies = | heavier than C30 |

TABLE 1

| time min | wt % olef/par | wt % ald/alc/for | wt % rev | wt % irrev | wt % acet | wt % heavies | olefin utilisation |
|---|---|---|---|---|---|---|---|
| 0 | 0.09 | 7.75 | 50.70 | 32.81 | 8.65 | 0.00 | 4.86 |
| 5 | 0.17 | 3.57 | 48.25 | 30.76 | 12.05 | 5.19 | 5.09 |
| 10 | 0.17 | 5.98 | 46.92 | 29.46 | 11.50 | 5.96 | 4.57 |
| 15 | 0.16 | 5.94 | 48.87 | 26.22 | 11.42 | 7.39 | 4.62 |
| 20 | 0.14 | 5.48 | 44.41 | 29.82 | 11.72 | 8.42 | 4.65 |
| 30 | 0.14 | 6.28 | 44.62 | 30.77 | 11.59 | 6.59 | 4.47 |
| 60 | 0.12 | 6.17 | 40.02 | 35.17 | 11.32 | 7.19 | 4.55 |
| 90 | 0.11 | 6.95 | 37.92 | 36.44 | 11.22 | 7.35 | 4.38 |
| 120 | 0.11 | 8.39 | 36.44 | 36.85 | 10.98 | 7.23 | 4.11 |
| 150 | 0.10 | 5.44 | 37.44 | 39.79 | 11.10 | 6.13 | 4.78 |
| 180 | 0.10 | 8.96 | 35.86 | 38.93 | 10.76 | 5.39 | 4.03 |
| FINAL | 0.10 | 10.77 | 36.39 | 44.22 | 8.52 | 0.00 | 4.09 |

TABLE 2

| time. min | wt % olef/par | wt % ald/alc/for | wt % rev | wt % irrev | wt % acet | wt % heavies | olefin utilisation |
|---|---|---|---|---|---|---|---|
| FEED | 0.13 | 7.90 | 47.73 | 31.71 | 12.53 | 0.00 | 3.89 |
| 0 | 0.48 | 8.22 | 54.47 | 24.31 | 12.52 | 0.00 | 3.86 |
| 60 | 0.44 | 7.94 | 51.04 | 29.12 | 12.46 | 0.00 | 3.91 |
| 90 | 0.37 | 7.42 | 54.79 | 24.77 | 12.65 | 0.00 | 3.98 |
| 120 | 0.32 | 7.30 | 51.24 | 28.49 | 12.66 | 0.00 | 3.99 |
| 150 | 0.31 | 7.24 | 54.07 | 24.94 | 12.64 | 0.00 | 4.02 |
| 180 | 0.25 | 7.06 | 51.54 | 28.54 | 12.61 | 0.00 | 4.05 |
| 240 | 0.21 | 6.85 | 55.05 | 25.13 | 12.76 | 0.00 | 4.07 |
| 300 | 0.17 | 6.66 | 51.75 | 28.89 | 12.52 | 0.00 | 4.15 |

TABLE 3

| time min | wt % olef/par | wt % ald/alc/for | wt % rev | wt % irrev | wt % acet | wt % heavies | olefin conversion | olefin utilisation |
|---|---|---|---|---|---|---|---|---|
| 0 | 50.06 | 3.06 | 25.65 | 16.88 | 4.34 | 0.00 | 0.00 | 11.92 |
| 5 | 32.64 | 17.01 | 24.85 | 11.83 | 7.94 | 5.75 | 32.85 | 3.48 |
| 10 | 23.15 | 24.29 | 24.18 | 12.15 | 9.56 | 6.67 | 51.34 | 2.52 |
| 15 | 17.72 | 27.05 | 23.91 | 12.55 | 11.60 | 7.16 | 62.30 | 2.18 |
| 20 | 14.05 | 27.88 | 23.85 | 12.85 | 13.62 | 7.76 | 69.89 | 2.01 |
| 30 | 10.88 | 26.48 | 20.72 | 14.88 | 17.44 | 9.58 | 76.53 | 1.88 |
| 60 | 8.17 | 21.65 | 20.49 | 15.39 | 23.40 | 10.90 | 82.34 | 1.82 |
| 90 | 5.06 | 15.31 | 19.67 | 17.70 | 29.38 | 12.88 | 89.01 | 1.82 |
| 120 | 5.05 | 20.68 | 18.81 | 20.51 | 25.17 | 9.78 | 88.96 | 1.77 |
| 150 | 4.27 | 31.05 | 18.13 | 25.41 | 15.71 | 5.42 | 90.53 | 1.73 |
| 180 | 4.56 | 40.54 | 18.22 | 28.72 | 7.86 | 0.00 | 89.79 | 1.66 |
| FINAL | 4.64 | 39.65 | 18.47 | 29.07 | 8.17 | 0.00 | 89.61 | 1.68 |

TABLE 4

| time min | wt % olef/par | wt % ald/alc/for | wt % rev | wt % irrev | wt % acet | wt % heavies | olefin conversion | olefin utilisation |
|---|---|---|---|---|---|---|---|---|
| 0 | 70.30 | 1.81 | 16.84 | 8.90 | 2.42 | 0.00 | 0.00 | 21.804 |
| 5 | 37.39 | 20.76 | 19.48 | 10.15 | 8.19 | 4.02 | 43.05 | 3.024 |
| 10 | 28.37 | 26.98 | 18.45 | 10.00 | 10.93 | 5.19 | 55.98 | 2.266 |
| 15 | 21.79 | 30.87 | 17.80 | 9.97 | 13.63 | 5.94 | 65.71 | 1.903 |
| 20 | 18.90 | 33.00 | 16.43 | 10.01 | 16.96 | 6.69 | 73.13 | 1.675 |
| 30 | 13.12 | 33.41 | 14.54 | 12.11 | 21.25 | 5.56 | 78.92 | 1.512 |
| 60 | 7.84 | 24.17 | 13.17 | 12.15 | 34.25 | 8.46 | 87.35 | 1.396 |
| 90 | 6.12 | 18.62 | 12.44 | 12.81 | 40.69 | 9.31 | 90.11 | 1.368 |
| 120 | 5.38 | 20.33 | 12.31 | 15.00 | 38.92 | 8.07 | 91.26 | 1.367 |
| 150 | 5.00 | 23.55 | 12.82 | 18.58 | 33.07 | 6.99 | 91.71 | 1.424 |
| 180 | 4.74 | 37.50 | 12.46 | 20.95 | 24.13 | 5.21 | 92.19 | 1.423 |
| FINAL | 6.14 | 46.57 | 10.93 | 19.86 | 14.09 | 2.40 | 89.84 | 1.333 |

TABLE 5

| time min | wt % olef/par | wt % ald/alc/for | wt % rev | wt % irrev | wt % acet | wt % heavies | olefin utilisation |
|---|---|---|---|---|---|---|---|
| 0 | 50.00 | 1.42 | 14.74 | 28.71 | 5.14 | 0.00 | 13.25 |
| 5 | 26.31 | 15.59 | 14.03 | 16.55 | 7.33 | 20.18 | 3.77 |
| 10 | 17.52 | 20.47 | 13.18 | 14.31 | 9.65 | 24.87 | 2.83 |
| 20 | 12.89 | 23.53 | 13.78 | 15.25 | 14.07 | 20.47 | 2.23 |
| 30 | 8.82 | 19.61 | 12.71 | 14.96 | 17.98 | 25.91 | 2.21 |
| 60 | 6.45 | 17.49 | 12.11 | 17.85 | 22.20 | 23.88 | 2.07 |
| 90 | 5.18 | 24.41 | 12.05 | 24.97 | 19.62 | 13.77 | 1.84 |
| 120 | 5.10 | 32.15 | 12.12 | 28.43 | 14.92 | 7.27 | 1.71 |
| 150 | 4.33 | 34.34 | 11.87 | 30.74 | 13.20 | 5.51 | 1.69 |
| 180 | 4.42 | 36.50 | 11.90 | 31.20 | 11.72 | 4.25 | 1.67 |
| FINAL | 4.92 | 42.20 | 11.82 | 33.04 | 7.99 | 0.02 | 1.60 |

TABLE 6

| time min | wt % olef/par | wt % ald/alc/for | wt % rev | wt % irrev | wt % acet | wt % heavies | olefin utilisation |
|---|---|---|---|---|---|---|---|
| 0 | 53.05 | 38.18 | 8.75 | 0.01 | 0.01 | 0.01 | 2.381 |
| 5 | 36.27 | 29.87 | 8.67 | 6.31 | 18.81 | 0.07 | 1.778 |
| 10 | 25.56 | 29.79 | 8.62 | 6.84 | 19.19 | 0.00 | 1.435 |
| 15 | 20.48 | 42.97 | 8.29 | 7.10 | 21.04 | 0.11 | 1.306 |
| 20 | 15.19 | 39.46 | 7.51 | 9.65 | 28.11 | 0.07 | 1.219 |
| 30 | 12.20 | 37.85 | 8.59 | 8.77 | 32.41 | 0.17 | 1.165 |
| 60 | 6.99 | 25.06 | 8.09 | 9.59 | 45.07 | 5.19 | 1.156 |
| 90 | 5.84 | 28.15 | 8.00 | 10.53 | 41.53 | 5.94 | 1.162 |
| 120 | 5.94 | 51.62 | 7.95 | 11.07 | 21.20 | 2.22 | 1.112 |
| 150 | 5.08 | 59.30 | 7.32 | 14.44 | 13.59 | 0.26 | 1.105 |
| 180 | 5.16 | 66.38 | 6.91 | 12.83 | 8.63 | 0.10 | 1.075 |
| FINAL | 4.96 | 63.89 | 6.97 | 12.95 | 9.75 | 1.48 | 1.096 |

TABLE 7

| time min | wt % olef/par | wt % ald/alc/for | wt % rev | wt % irrev | wt % acet | wt % heavies | olefin utilisation |
|---|---|---|---|---|---|---|---|
| 0 | 90.01 | 0.60 | 5.62 | 2.97 | 0.81 | 0.00 | |
| 5 | 56.85 | 31.41 | 5.00 | 2.79 | 3.08 | 0.87 | 2.646 |
| 10 | 37.20 | 38.41 | 6.57 | 5.34 | 9.93 | 2.55 | 1.805 |
| 15 | 26.93 | 42.34 | 7.12 | 6.86 | 14.22 | 2.54 | 1.506 |
| 20 | 22.17 | 44.84 | 6.05 | 6.28 | 17.61 | 3.05 | 1.349 |
| 30 | 16.07 | 41.89 | 5.12 | 7.13 | 25.48 | 4.32 | 1.232 |
| 60 | 12.54 | 39.49 | 5.44 | 6.55 | 30.80 | 5.19 | 1.172 |
| 90 | 10.38 | 32.09 | 5.53 | 7.20 | 38.16 | 6.64 | 1.167 |
| 120 | 8.81 | 29.82 | 5.38 | 8.79 | 40.44 | 6.75 | 1.161 |
| 150 | 8.07 | 39.36 | 5.17 | 11.89 | 30.07 | 5.45 | 1.172 |
| 180 | 7.52 | 47.54 | 5.17 | 13.82 | 22.16 | 3.80 | 1.164 |
| FINAL | 8.12 | 49.14 | 5.15 | 14.34 | 20.23 | 3.02 | 1.171 |

TABLE 8

| time min | wt % olef/par | wt % ald/alc/for | wt % rev | wt % irrev | wt % acet | wt % heavies | olefin utilisation |
|---|---|---|---|---|---|---|---|
| 0 | 50.00 | 0.02 | 49.37 | 0.00 | 0.62 | 0.00 | |
| 5 | 30.71 | 17.83 | 47.44 | 0.00 | 1.89 | 2.13 | 4.472 |
| 10 | 17.94 | 22.64 | 51.17 | 0.00 | 4.13 | 4.11 | 3.206 |
| 15 | 14.05 | 22.47 | 53.28 | 0.00 | 6.18 | 4.01 | 2.966 |
| 20 | 12.34 | 27.60 | 49.79 | 0.00 | 6.96 | 3.31 | 2.445 |
| 30 | 8.27 | 21.45 | 52.27 | 0.00 | 12.97 | 5.03 | 2.426 |
| 60 | 5.95 | 17.49 | 52.77 | 0.00 | 18.22 | 5.58 | 2.321 |
| 90 | 4.91 | 20.41 | 54.23 | 0.00 | 16.44 | 4.01 | 2.245 |
| 120 | 4.40 | 26.86 | 50.19 | 5.22 | 11.11 | 2.22 | 2.172 |
| 150 | 4.10 | 31.16 | 50.03 | 5.70 | 7.62 | 1.39 | 2.128 |
| 180 | 3.89 | 34.36 | 50.01 | 5.91 | 5.09 | 0.74 | 2.093 |
| FINAL | 4.25 | 38.87 | 49.36 | 5.90 | 1.61 | 0.00 | 2.043 |

I claim:

1. In the method of producing higher alcohols by the hydroformylation in an oxonation reactor of $C_4$–$C_{16}$ olefins in which the olefins are hydroformylated to produce an oxonation product primarily comprised of aldehydes, alcohols and formate esters, the product of oxonation is hydrogenated to provide a product mixture comprising higher alcohols, a high boiling fraction and a low boiling fraction, the high boiling fraction and low boiling fraction are subjected to distillation, the high boiling fraction (heavy oxo fraction) is subjected to cracking (HOF cracking) in which Irreversible products comprising ether-aldehydes and ether-alcohols are cracked to aldehydes and alcohols which are distilled overhead and Reversible products comprising unsaturated and hydrogenated ethers which are not converted remain in the cracking reactor as bottoms product (U-HOF), such U-HOF bottoms product comprising ether and ether-alcohol dimers and acetal trimers, the improvement which comprises the steps of (1) distilling the U-HOF bottoms product to recover the ether-alcohol dimers and (2) recirculating said ether-alcohol dimers to the oxonation reactor thereby converting said ether-alcohols to ether-aldehydes.

2. The process of claim 7 wherein the olefins are $C_6$–$C_{12}$ olefins.

* * * * *